(12) United States Patent
Hardy, III

(10) Patent No.: US 7,392,658 B1
(45) Date of Patent: Jul. 1, 2008

(54) AUTOMATED AIR CONDITIONER DRAIN LINE CLEAN-OUT SYSTEM

(76) Inventor: William G. Hardy, III, 2508 Windsor Forest Dr., Louisville, KY (US) 40272

( * ) Notice: Subject to any disclaimer, the term of this patent is extended or adjusted under 35 U.S.C. 154(b) by 0 days.

(21) Appl. No.: 11/870,621

(22) Filed: Oct. 11, 2007

Related U.S. Application Data

(63) Continuation of application No. 11/775,434, filed on Jul. 10, 2007, which is a continuation-in-part of application No. 11/696,985, filed on Apr. 5, 2007.

(60) Provisional application No. 60/746,304, filed on May 3, 2006.

(51) Int. Cl.
*A23L 3/36* (2006.01)
*F24F 3/16* (2006.01)
*B08B 3/00* (2006.01)

(52) U.S. Cl. ............... 62/78; 62/303; 62/474; 137/15.05; 137/240

(58) Field of Classification Search ........ 62/78, 62/149, 298, 303, 322, 324.4, 474; 137/240, 137/15.05
See application file for complete search history.

(56) References Cited

U.S. PATENT DOCUMENTS 4,789,467 A * 12/1988 Lindsay et al. ............ 210/103
4,937,559 A    6/1990 Meacham et al.
4,962,778 A * 10/1990 Driskill .................. 134/169 C
5,004,025 A    4/1991 Robbins
5,514,344 A    5/1996 D'Agaro
5,722,458 A    3/1998 Potter
6,182,677 B1 * 2/2001 Pignataro ................ 137/15.05
6,427,458 B1   8/2002 Fowler
6,442,956 B1   9/2002 Herren
6,487,867 B1  12/2002 Herren
6,701,740 B1 * 3/2004 Hernandez-Zelaya ....... 62/291
6,708,717 B1   3/2004 Coogle
6,892,907 B2   5/2005 Varney
2004/0250841 A1 12/2004 Kimbrough et al.
2005/0138939 A1 6/2005 Spanger
2006/0096307 A1 5/2006 Coogle
2007/0119503 A1 5/2007 Scaringe

FOREIGN PATENT DOCUMENTS

WO    WO2005075895 A1    8/2005

* cited by examiner

*Primary Examiner*—Marc E Norman
(74) *Attorney, Agent, or Firm*—Camoriano and Associates; Theresa Camoriano; Guillermo Camoriano

(57) ABSTRACT

A cleaning system for an air conditioner injects a biocide followed at regular intervals, which may be followed by a rinsing flush.

11 Claims, 6 Drawing Sheets

AUTOMATED AIR CONDITIONER DRAIN LINE CLEAN-OUT SYSTEM

This application is a continuation of U.S. patent application Ser. No. 11/775,434, filed Jul. 10, 2007, which is a continuation-in-part of U.S. patent application Ser. No. 11/696,985, filed Apr. 5, 2007 which claims priority from U.S. Provisional Application Ser. No. 60/746,304 filed May 3, 2006, which is hereby incorporated herein by reference.

BACKGROUND

The present invention relates to air conditioning systems, and, in particular, to an automated system for cleaning out the drain line of an air conditioning system to prevent the build-up of algae or other growth.

Every year millions of dollars are spent to repair the damage done from clogged and overflowing evaporator drain lines and pans. The average air conditioning unit produces between five and eight gallons a day of condensate when in operation. If the drain line is clogged, it does not take long to overflow the drain pan and cause considerable damage to flooring, ceiling, carpet, as well as possible damage to adjacent housing units. There also can be significant cost from mold and mildew damage. This damage often is not covered by insurance.

The key to prevention is having the drain lines treated on a regular basis with bleach or some other biocide fluid. The problem is getting the treatment done on a regularly scheduled basis. In 2004, almost forty percent of home purchases were second homes for investment or vacation properties. This absentee ownership adds to the problem of scheduled maintenance or the detection of a problem before it can cause any damage. According to the UN Atlas of the Oceans, forty-four percent of the world's population lives within 150 kilometers of a coastline. In the United States, around fifty-three percent of the population lives within 50 miles of the oceans, and since 1970 there have been approximately 2000 homes per day erected in coastal areas. This means that there is an ever-increasing number of homes which are subjected to high humidity and need algae protection for their air conditioner evaporator drain lines.

Prior art devices for dealing with the algae build-up in the evaporator portion of the air conditioning unit have several limitations, including the following:

The devices add a trickle amount of biocide to the drain pan of the evaporator on a continuous basis or on an intermittent but frequent basis. This small amount of flow over the large area of the drain pan results in a very low flow velocity, which is insufficient to wash away any solids.

Because the biocide is added on a continuous basis (or on an intermittent but frequent basis), the storage tank holding the biocide is promptly depleted, requiring frequent refilling by the user. If the user is absent for an extended period of time, the device does not get refilled and problems ensue.

The biocide is present on a continuous basis over the large exposed area of the drain pan. This results in objectionable odors during operation, as well as the presence of fumes which may damage parts of the air conditioning unit.

SUMMARY

An example of a system that helps solve the potential of property damage and expensive repairs is described below. That system provides automated, scheduled applications of a biocide (and, if desired, an additional flushing solution) into the evaporator drain line.

DETAILED DESCRIPTION

Figure 1:
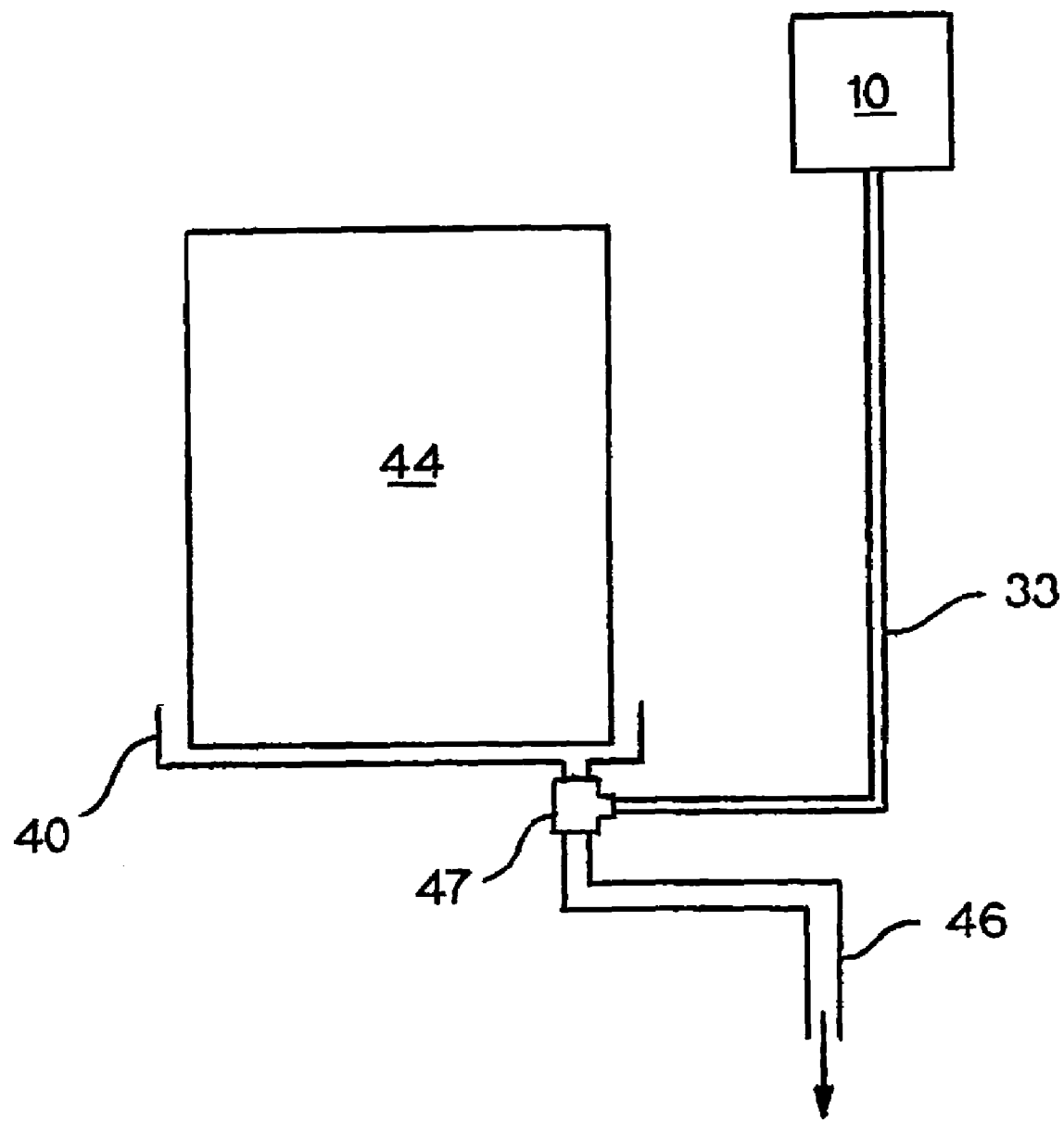
FIG. 1 is a schematic of a system made in accordance with the present invention, in a typical installation with an A/C evaporator.
Figure 5:
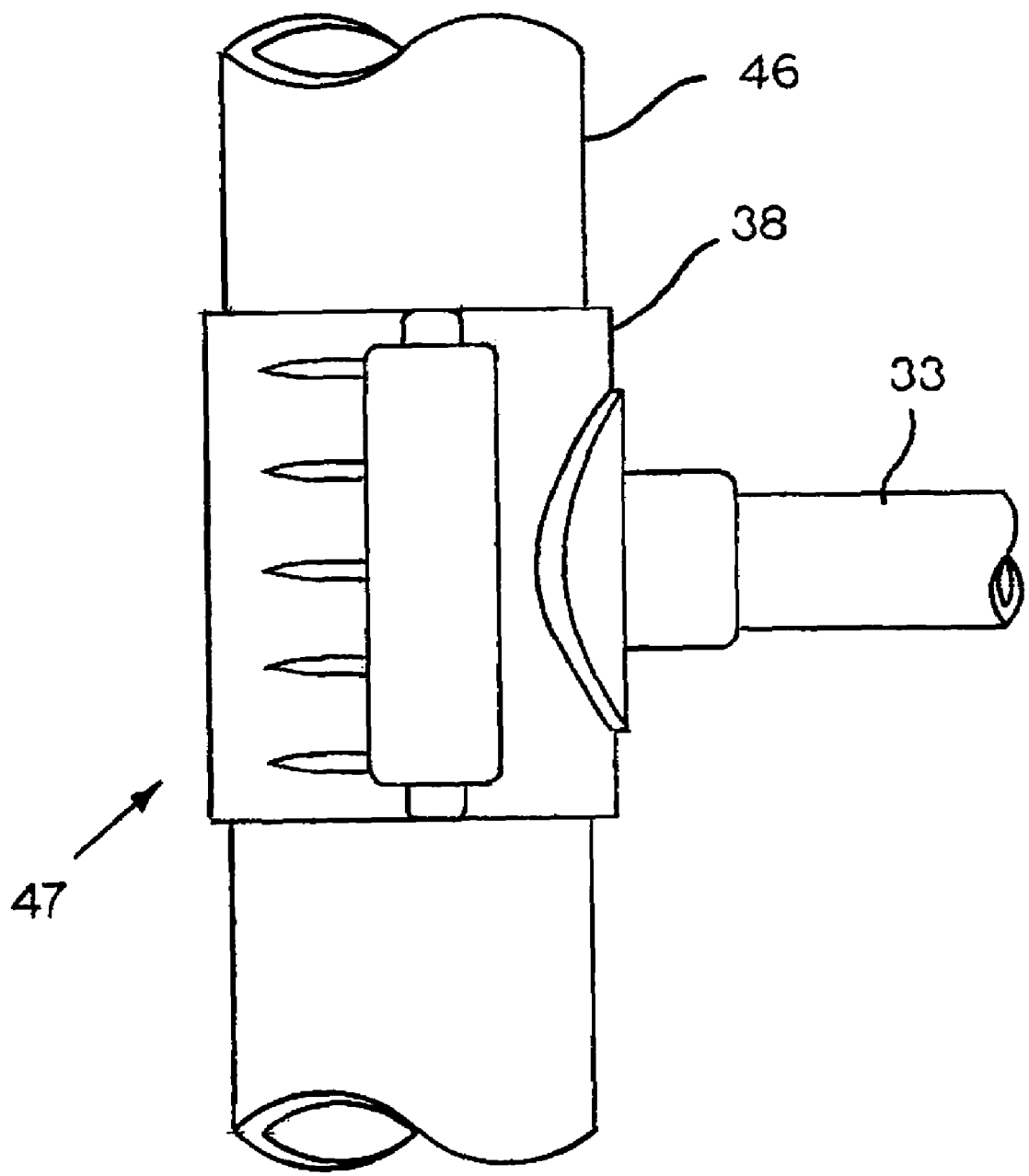
FIG. 5 is a broken-away view of an injection saddle for connecting the biocide line to the drain line as shown in FIG. 1.
Figure 6:
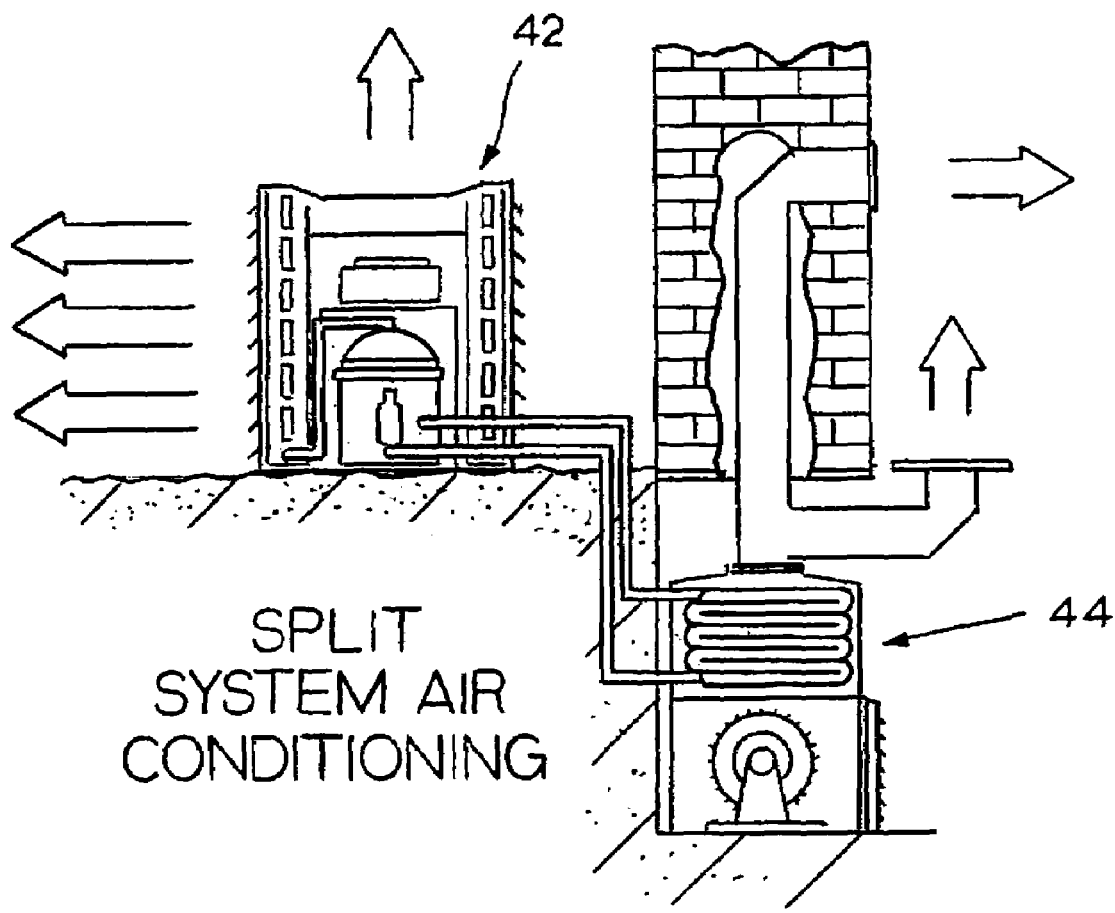
FIG. 6 is a sketch of a split system air conditioner showing the location of the air handling unit where the evaporator is typically located.

FIGS. 1-6 show one example of an evaporator drain clean-out system 10 made in accordance with the present invention. Referring briefly to FIG. 6, a split system air conditioner typically includes a condensing unit 42 installed outside of the home or building, and an air handling unit 44, which is also referred to as the evaporator unit, installed inside the home or building. Referring now to FIG. 1, the evaporator unit 44 typically has an evaporator drain pan 40 at a first elevation, which catches the water that condenses on the evaporator coils as the air in the house is cooled. The water which collects in the drain pan 40 is routed by gravity to a drain via the drain line 46.

The drain line 46 is an ideal place for algal growth, since it is moist and has low fluid flow rates. An automated cleaning system 10, made in accordance with the present invention, and described in more detail below, keeps this drain line 46 clean and unobstructed to prevent clogging of the line 46. If the line 46 were to clog, the condensate from the evaporator 44 could back up until it overflowed the drain pan 40, which could cause water damage to the home or building.

This particular cleaning system 10 ensures protection for a 360 day period against clogging of the drain line 46. As described in more detail below, the system 10 includes a continuous thirty-day timer housed in a control unit 20, which then resets after the process is completed. It also includes tanks 18 to hold a biocide solution and a flushing solution, and these tanks 18 only need to be filled every 360 days, such that the problem of absentee ownership with sporadic visits for treatment is alleviated if not totally eliminated.

The cleaning system 10 described herein automatically releases one cup (or any desired amount) of bleach (or some other biocide solution) into the evaporator drain line 46 and follows it with a flush of a cup (or any desired amount) of water or other flushing fluid at desired intervals, such as once each month, The particular embodiment described herein is intended to work on thirty-day intervals and holds sufficient fluid that it only requires refilling once every 360 days. Of course, the intervals of operation the size of the fluid reservoirs, and the amount of fluid that is released at each interval may be changed, as desired.

Figure 2:
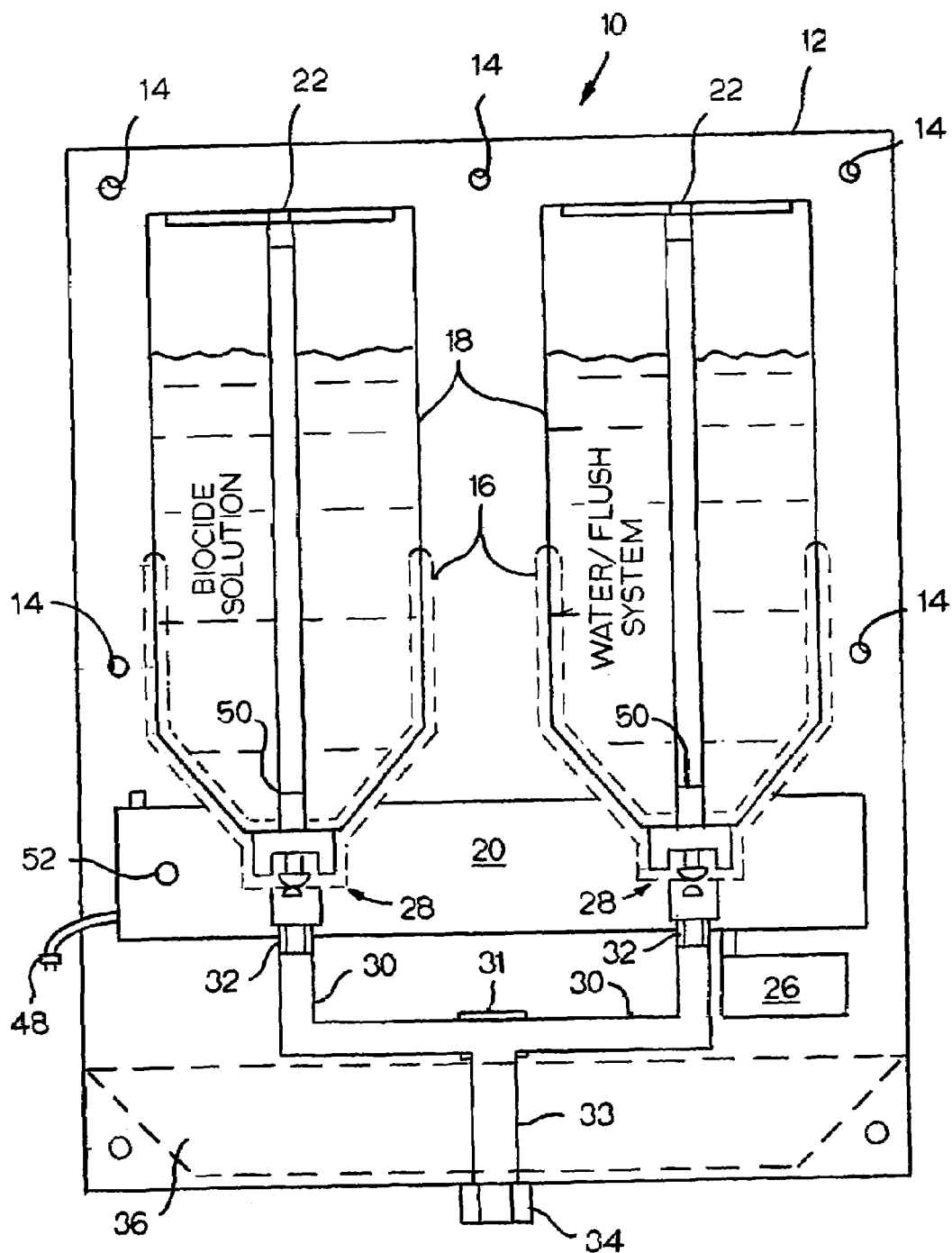
FIG. 2 is a front view of the clean-out system of FIG. 1.

Referring to FIG. 2, this system 10 is housed in a compact package measuring 15 inches wide, by 22 inches tall, by 6 inches deep. The mostly plastic construction makes for a lightweight unit 10. The unit 10 includes a mounting station 12, which has holes 14 pre-drilled for securing the unit 10 to a wall or to the air handler of the A/C unit itself. On the mounting station 12 there are two tank cradle racks 16 (shown in dotted lines for clarity), each holding one twelve-cup capacity plastic dispenser tank 18. Each tank 18 is approximately 13 inches long and has a square cross-section of 4 inches by 4 inches. This particular embodiment 10 utilizes tanks 18 with a 12-cup capacity such that each tank holds enough fluid for 12 monthly flushings of 1 cup per month. Larger or smaller capacity tanks 18 may be used if desired.

Each tank 18 has a one-way valve 22 on top to let air in as fluid is evacuated, without allowing any odors out or allowing significant evaporation. The tops of the plastic tanks 18 are hinged at 24 (See also FIG. 4) so they can be opened to facilitate refilling of the tanks 18 (providing a closable fill opening), and they are ribbed internally and fit against the tanks' interiors to ensure a tight seal. Other known types of tops could be used, such as a screw-on lid, if desired. A gasket may be used to seal the top against the rest of the tank, if desired.

Also included in the cleaning unit 10 is a control unit 20 which contains the power controls 52, a power cord 48, and a 30-day interval on/off recycling timer control. The timer times down the 30 day interval, after which it sends a signal to sequentially open valves 28 at the bottom (outlet end) of the tanks 18. While these drawings show a particular type of valve 28, various types of valves could be used, such as solenoid valves, which, for example, would open when energized by the control unit 20 and would then close when the control unit 20 de-energizes the valve 28.

A power back-up unit 26 includes batteries to power the timer and control system in case of a power outage. Of course, the cleaning device 10 could be entirely battery powered, in which case it would not need to be plugged into an outlet via the power cord 48. Alternatively, it could be powered by rechargeable batteries, which are continuously recharged by being plugged into an outlet.

Figure 3:
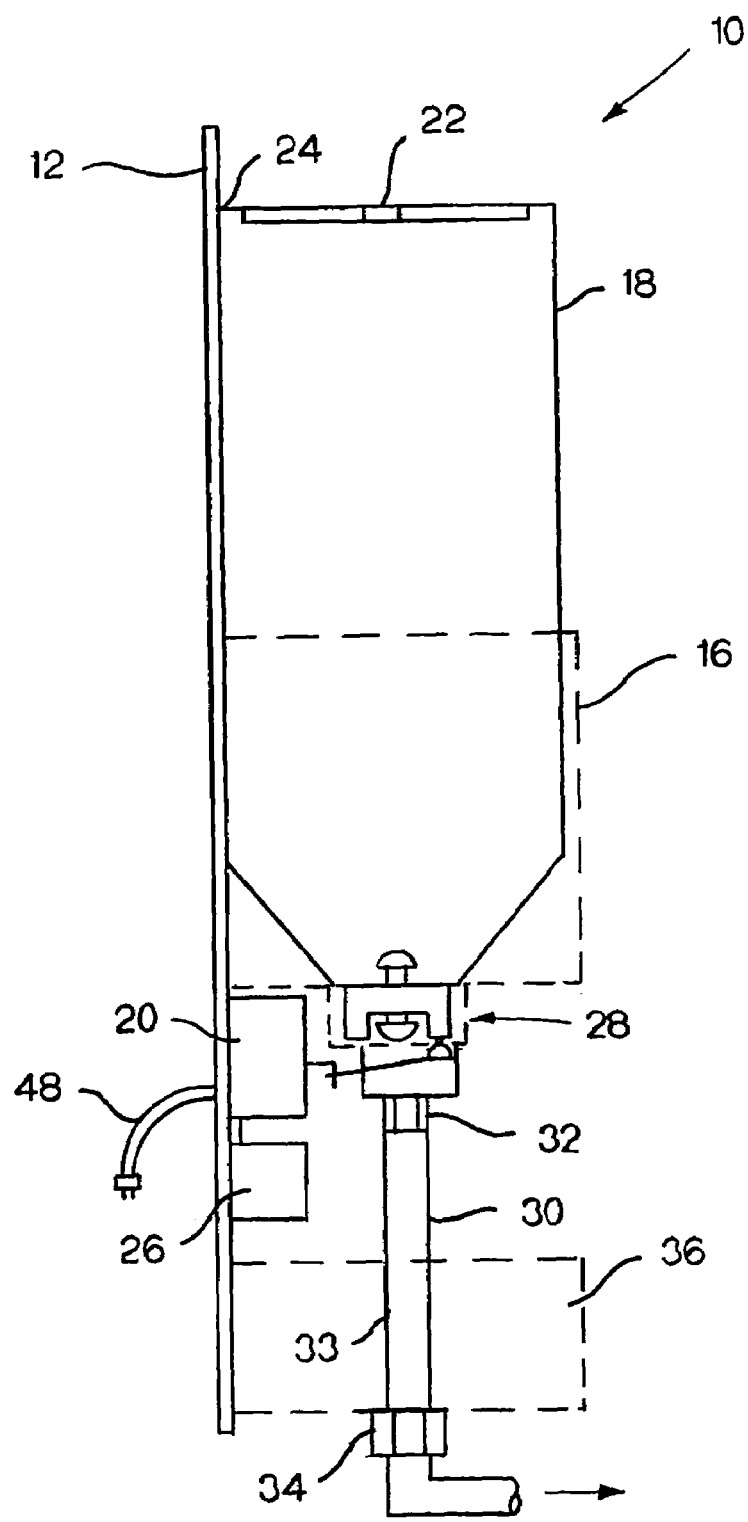
FIG. 3 is a side view of the clean-out system of FIG. 1.
Figure 4:
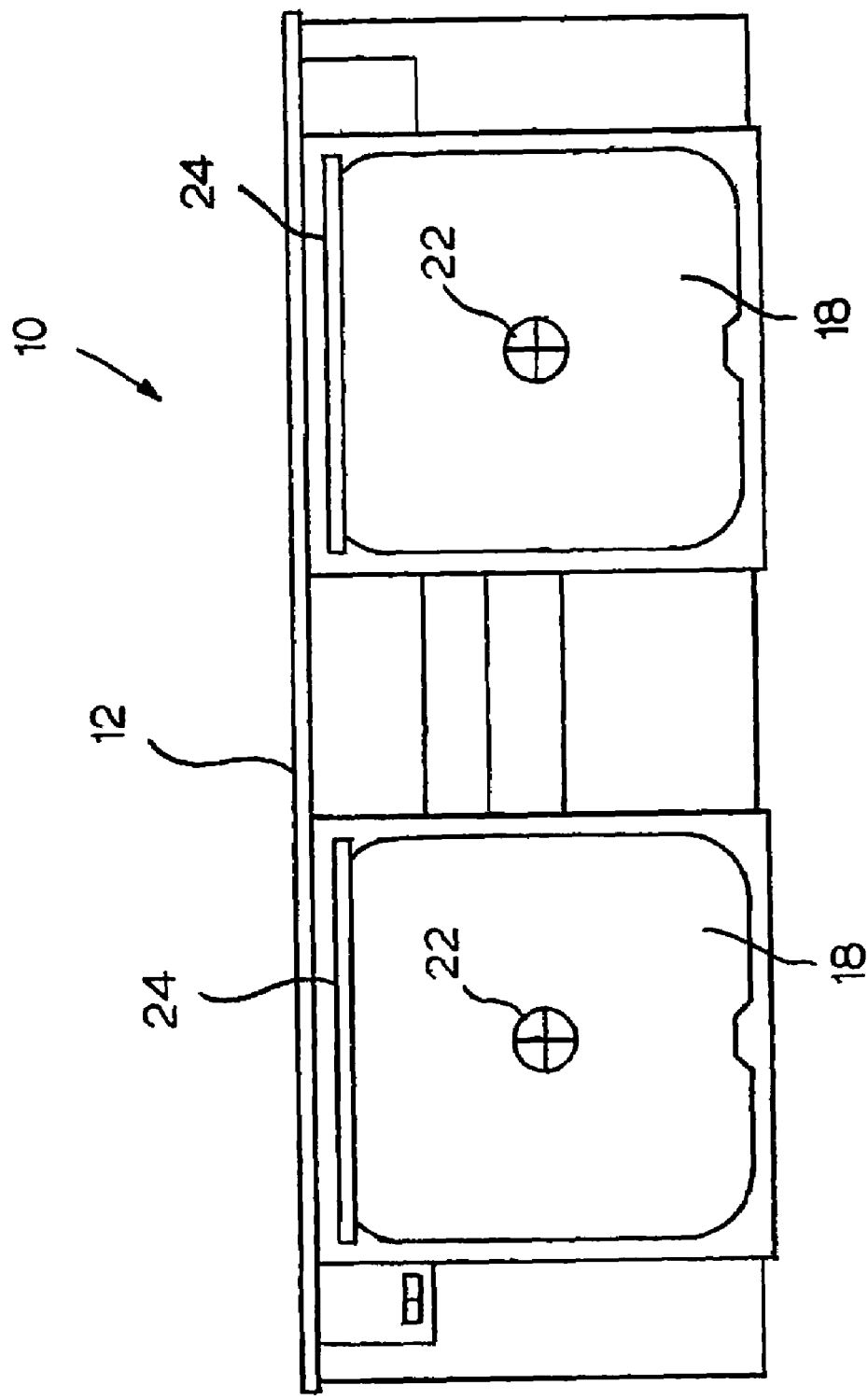
FIG. 4 is a plan view of the clean-out system of FIG. 1.

As best appreciated in FIGS. 2 and 3, a catch pan 36 (shown in dotted lines for clarity) is mounted to the mounting station 12, and is disposed so as to catch any liquid which may fall or leak out of the tanks 18 (particularly when these tanks 18 are being refilled).

A ⅜ inch tubing line 30 connects to the outlet of each of the valves 28 (via a tubing compression fitting 32), as depicted in FIG. 2. These lines 30 extend downwardly and join together to form a single cleaning solution line 33 at a "T" 31. This cleaning solution line 33 extends downwardly through a bulkhead fitting 34 at the bottom of the catch pan 36 (see also FIG. 3) and goes on to connect to the drain line 46 at an inlet point 47 which is below the elevation of the drain pan 40 and adjacent the connection of the drain line 46 to the drain pan 40, as depicted in FIG. 1. The lines 30 and 33 provide an enclosed fluid path from the containers 18 to the inlet 47 of the drain line 46.

FIG. 5 shows a typical connection of the cleaning solution line 33 to the evaporator drain line 46 using a saddle clamp 38. Other mechanisms for connecting the cleaning solution line 33 to the evaporator drain line to 46 may be used instead of a saddle clamp, such as the use of a "T" in the line 46. Preferably, the inlet connection 47 of the cleaning solution line 33 to the evaporator drain line 46 is located immediately downstream of the junction of the evaporator drain line 46 and the evaporator drain pan 40.

As shown in FIG. 1, the cleaning system 10 is mounted at an elevation higher than the elevation of the evaporator pan 40 and higher than the elevation of the inlet 47 where the line 33 connects to the drain line 46, so gravity assists in transferring the fluids from the tanks 18 to the drain line 46. It is desirable to ensure that the unit 10 is squarely mounted and located above the drain line 46, but not so high as to make it difficult for the user to refill the tanks 18.

Prior to initial operation, one tank 18 is filled with water (one may add a capful of bleach to avoid algae growth in this flush water tank), and the other tank 18 is filled with bleach or some other biocide solution.

Once the unit 10 is installed, with its cleaning solution line 33 properly connected to the drain line 46, the tanks 18 filled with a biocide solution and a flushing solution respectively, and the cleaning system 10 is powered up (either through the battery backup 26 or the power cord 48), the start button 52 may be depressed for an initial treatment. The cleaning system 10 will then continue to operate automatically for regular treatments spaced 30 days apart. Since this system 10 holds enough fluid for twelve treatments, it can provide continuous treatment for a 360-day period without the expense of repeated technician service calls. If the fluid tanks are refilled periodically before they run out of fluid, the system can continue to work for a much longer period of time. The system works even when the dwelling is un-occupied to prevent clogs from forming over an extended period. The installation is easy and does not require the costs of a professional installer.

During operation, the control unit 20 sends a signal to open a first valve 28 for a preset time period to release approximately 1 cup of biocide solution from a first tank 18. The biocide solution travels from the first tank 18 through the tubing 30 and on through the cleaning solution line 33 until it is injected into the evaporator drain line 46 at the inlet point 47 adjacent the evaporator drain pan 40. After a 3 to 5 minute delay, the control unit 20 sends a signal to open a second valve 28, also for a preset time period, to release approximately 1 cup of flushing solution from the second tank 18. As was the case with the biocide, this flushing solution is transferred via the tubing 30 and the cleaning solution line 33 until it is also injected into the evaporator drain line 46 at the inlet point 47. The control timer in the control unit 20 then resets itself and begins a new thirty-day countdown before it repeats the process again.

The sudden injection of a substantial amount of biocide directly into the drain line 46 every 30 days results in a concentrated treatment of the drain line 46. Furthermore, because the volume of fluid is injected directly into the drain line 46 and is done so in one "slug" (instead of a slow trickle delivered over a large area of the evaporator drain pan), the velocity of the fluid flow of the biocide is high enough to wash away any slime or grime which may be fouling the wall of the drain line 46. If the biocide injection is followed by an injection of a flush solution, such as water, the biocide itself and any odors or fumes resulting from the biocide are flushed away together with any remaining algal growth, leaving a clean and unobstructed drain line 46.

The cleaning system 10 is uncomplicated such that anyone can operate it. The cleaning system 10 should therefore eliminate the need for repeated expensive visits by a skilled technician. The fluid level line 50 (See FIG. 2) in the tanks 18 makes it obvious when refilling is needed.

The embodiment described above is only one example of a product that can carry out the present invention. For example, instead of using gravity to feed the biocide and rinse fluid to the drain line 46, pumps (not shown) could be provided to pump the fluid from the tanks 18, in which case, the control system would be turning the pumps on and off to deliver the biocide and rinse water instead of opening and closing the valves.

It will be obvious to those skilled in the art that modifications may be made to the embodiments described above without departing from the scope of the present invention as claimed.

What is claimed is:

1. An automated system for cleaning out the evaporator drain line of an air conditioner, comprising:
    an evaporator drain pan at a first elevation;
    an evaporator drain line in fluid communication with said evaporator drain pan;
    a first container holding a first volume of biocide;
    a first enclosed fluid path from said first container to the evaporator drain line, said first enclosed fluid path connecting to said evaporator drain line at an elevation below said first elevation; and
    a first valve controlling fluid flow between said first container and said evaporator drain line; and further comprising a control system which periodically opens and closes said first valve.

2. An automated system for cleaning out the evaporator drain line of an air conditioner as recited in claim 1, and further comprising:
    a second container holding a rinse liquid;
    a second enclosed fluid path from said second container to the evaporator drain line at an elevation below said first elevation;
    a second valve controlling fluid flow between said second container and said evaporator drain line; and
    a control system which opens and closes said second valve shortly after each closing of the first valve.

3. An automated system for cleaning out the evaporator drain line of an air conditioner as recited in claim 2, wherein the first and second enclosed fluid paths join together and enter the evaporator drain line at the same point.

4. An automated system for cleaning out the evaporator drain line of an air conditioner as recited in claim 1, and further comprising a battery which powers said control system.

5. An automated system for cleaning out the evaporator drain line of an air conditioner as recited in claim 4, and further comprising a catch pan located below said first container.

6. An automated system for cleaning out the evaporator drain line of an air conditioner as recited in claim 1, wherein said first valve is actuated by said control system approximately once every 30 days.

7. An automated system for cleaning out the evaporator drain line of an air conditioner as recited in claim 1, wherein said first container has an outlet to said enclosed fluid path and a closable fill opening separate from said outlet.

8. An automated system for cleaning out the evaporator drain line of an air conditioner as recited in claim 7, wherein a one-way valve is mounted on said first container near the top in order to permit air to enter the container as biocide leaves through said outlet.

9. A method for cleaning out the evaporator drain line of an air conditioner having an evaporator drain pan at a first elevation, comprising the steps of:
    mounting a first container holding a first volume of biocide;
    connecting a first enclosed fluid path from said first container to an inlet to the evaporator drain line at an elevation below said first elevation;
    providing means for opening and closing fluid communication through said first enclosed fluid path; and
    automatically opening and closing said means at desired intervals to allow biocide to flow from said first container to said evaporator drain line.

10. A method for cleaning out the evaporator drain line of an air conditioner as recited in claim 9, wherein said first container is mounted at an elevation above said first elevation, said means is a valve, and said biocide flows by gravity from said first container to said evaporator drain line.

11. A method for cleaning out the evaporator drain line of an air conditioner as recited in claim 10, and further comprising the steps of:
    mounting a second container at an elevation above said first elevation, with a second enclosed fluid path from said second container to an inlet of said evaporator drain line at an elevation below said first elevation;
    providing a second valve in said second enclosed fluid path; and
    automatically opening and closing said second valve shortly after each time the first valve is opened and closed.

\* \* \* \* \*